(12) United States Patent
Harmon et al.

(10) Patent No.: US 7,834,335 B2
(45) Date of Patent: Nov. 16, 2010

(54) HAND HELD STERILIZATION DEVICES

(75) Inventors: Nicholas Harmon, Waitsfield, VT (US); Ryan Douglas, Stillwater, MN (US)

(73) Assignee: Verilux, Inc., Waitsfield, VT (US)

( * ) Notice: Subject to any disclaimer, the term of this patent is extended or adjusted under 35 U.S.C. 154(b) by 201 days.

(21) Appl. No.: 12/290,116

(22) Filed: Oct. 27, 2008

(65) Prior Publication Data

US 2010/0102252 A1    Apr. 29, 2010

(51) Int. Cl.
*A61L 2/10* (2006.01)
*G01N 21/33* (2006.01)
(52) U.S. Cl. .............................. 250/504 H; 250/504 R; 250/455.11; 250/493.1; 422/24; 422/186.3
(58) Field of Classification Search ............. 250/504 R, 250/504 H, 455.11, 493.1; 422/24, 186.3
See application file for complete search history.

(56) References Cited

U.S. PATENT DOCUMENTS

| | | | |
|---|---|---|---|
| 2,632,912 A | 3/1953 | Cuddeback | |
| 2,648,396 A | 8/1953 | Kirby | |
| 2,681,467 A | 6/1954 | Guyer | |
| 3,970,856 A | 7/1976 | Mahaffey et al. | |
| 3,975,790 A | 8/1976 | Patterson | |
| 4,952,369 A | 8/1990 | Belilos | |
| 5,233,283 A | 8/1993 | Kennedy | |
| 5,259,380 A | 11/1993 | Mendes et al. | |
| 5,420,768 A | 5/1995 | Kennedy | |
| 5,500,009 A | 3/1996 | Mendes et al. | |
| 5,634,711 A | 6/1997 | Kennedy et al. | |
| 5,728,090 A | 3/1998 | Martin et al. | |
| 5,783,909 A | 7/1998 | Hochstein | |
| 5,920,075 A | 7/1999 | Whitehead | |
| 5,968,455 A | 10/1999 | Brickley | |
| 6,063,108 A | 5/2000 | Salansky et al. | |
| 6,239,442 B1 | 5/2001 | Iimura | |
| 6,242,753 B1 * | 6/2001 | Sakurai | 250/504 R |
| 6,283,956 B1 | 9/2001 | McDaniel | |
| 6,443,978 B1 | 9/2002 | Zharov | |
| 6,656,424 B1 | 12/2003 | Deal | |
| 6,911,177 B2 | 6/2005 | Deal | |
| 6,953,940 B2 * | 10/2005 | Leighley et al. | 250/455.11 |
| 6,976,984 B2 | 12/2005 | Cense et al. | |
| 7,173,254 B2 | 2/2007 | Sauska et al. | |
| 7,175,806 B2 | 2/2007 | Deal et al. | |
| 7,201,765 B2 | 4/2007 | McDaniel | |
| 2004/0244138 A1 | 12/2004 | Taylor et al. | |
| 2005/0055070 A1 | 3/2005 | Jones et al. | |
| 2005/0065579 A1 | 3/2005 | Chen et al. | |
| 2005/0149150 A1 | 7/2005 | McDaniel | |

(Continued)

FOREIGN PATENT DOCUMENTS

WO    2005/011755 A2    2/2005

*Primary Examiner*—Nikita Wells
(74) *Attorney, Agent, or Firm*—Dardi & Herbert, PLLC

(57) ABSTRACT

Convenient mobile sterilization devices are described herein that, in certain embodiments, provide secure storage in a niche in a protective housing and one-button action to automatically deploy and activate the device for quick and powerful destruction of germs on a surface using one hand. Users can hold the UV-light device and move it across a target surface to sterilize or disinfect the surface. The device may be compact, easily deployed, provided with a durable cover for secure storage, and equipped with safety shut-off features to prevent unwanted uses.

16 Claims, 15 Drawing Sheets

U.S. PATENT DOCUMENTS

| | | |
|---|---|---|
| 2005/0228463 A1 | 10/2005 | Mac et al. |
| 2005/0234383 A1 | 10/2005 | Dougal |
| 2005/0261750 A1 | 11/2005 | McDaniel |
| 2006/0185116 A1 | 8/2006 | Lee et al. |
| 2006/0185117 A1 | 8/2006 | Seo et al. |
| 2006/0236496 A1 | 10/2006 | Oh et al. |
| 2006/0278088 A1 | 12/2006 | Helsel |
| 2006/0293727 A1 | 12/2006 | Spooner et al. |
| 2007/0023710 A1 | 2/2007 | Tom et al. |
| 2007/0032843 A1* | 2/2007 | Hsu .................... 607/88 |
| 2007/0067943 A1 | 3/2007 | Makarov |
| 2007/0129778 A1 | 6/2007 | Dougal |
| 2007/0167999 A1 | 7/2007 | Breden et al. |
| 2007/0185553 A1 | 8/2007 | Kennedy |
| 2007/0192986 A1 | 8/2007 | Garcia et al. |
| 2007/0209143 A1 | 9/2007 | Choi et al. |
| 2007/0209144 A1 | 9/2007 | Fester et al. |
| 2007/0231193 A1 | 10/2007 | Jung et al. |
| 2008/0004611 A1 | 1/2008 | Houbolt et al. |
| 2008/0052872 A1 | 3/2008 | Cho |
| 2008/0103563 A1 | 5/2008 | Powell et al. |
| 2008/0140164 A1 | 6/2008 | Oberreiter et al. |
| 2009/0240310 A1 | 9/2009 | Kennedy |
| 2010/0104471 A1* | 4/2010 | Harmon et al. ............... 422/24 |

* cited by examiner

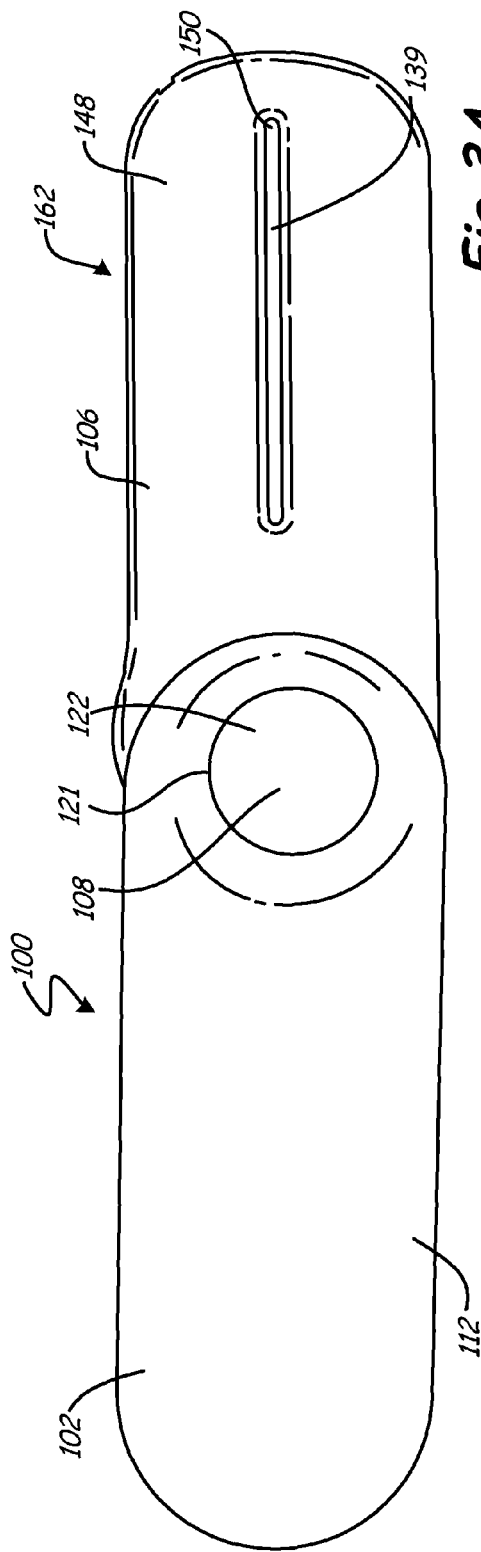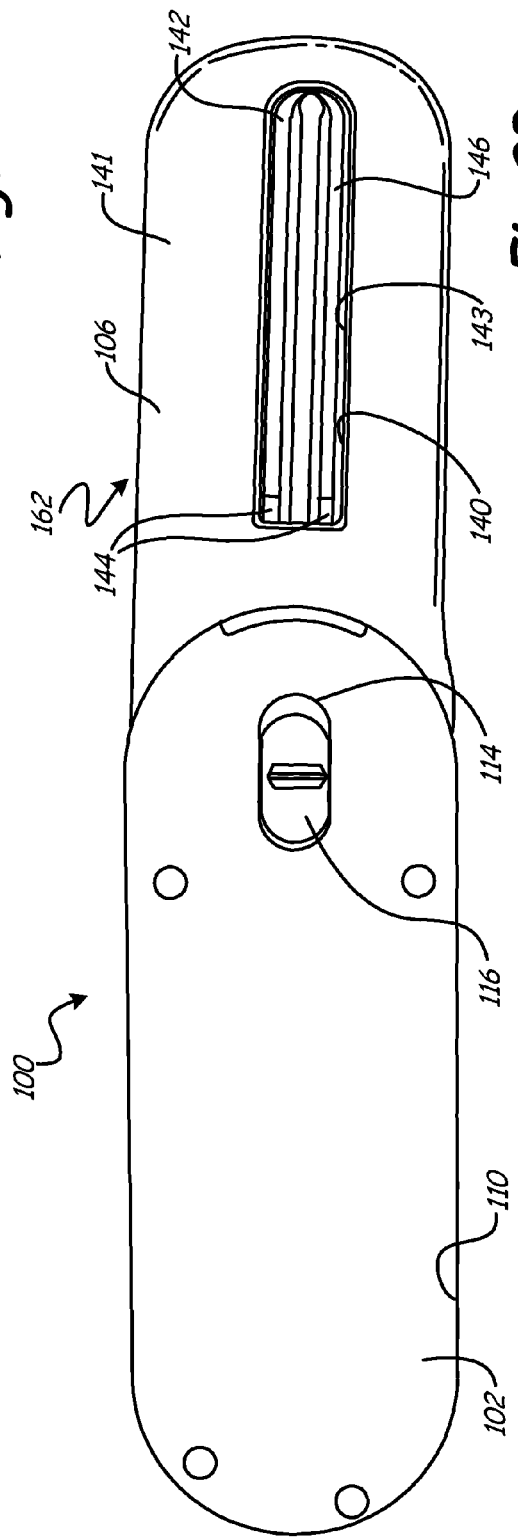

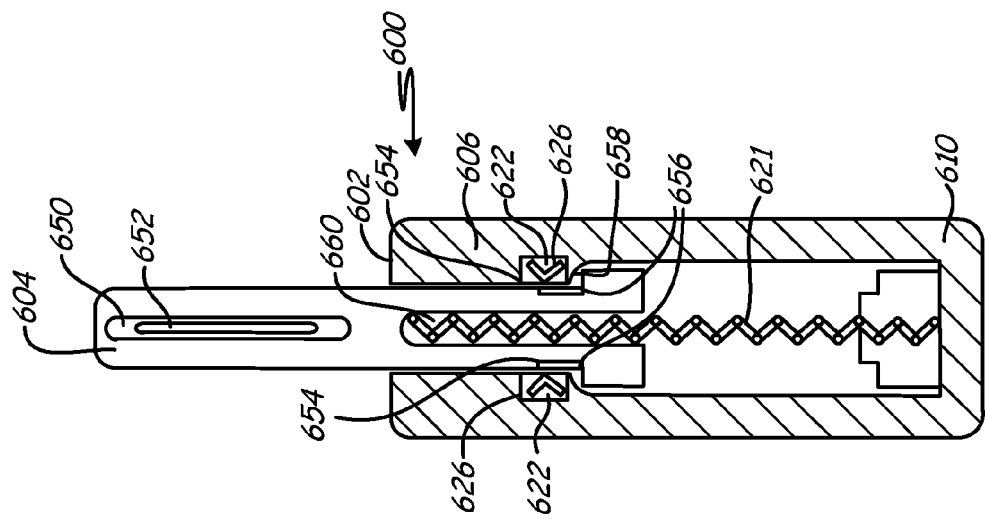
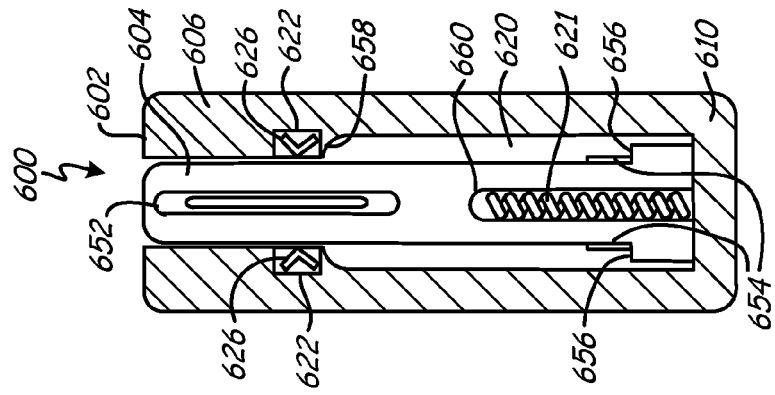
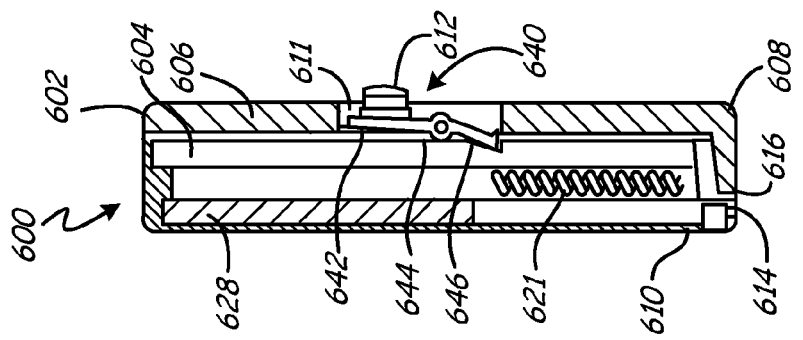

HAND HELD STERILIZATION DEVICES

TECHNICAL FIELD

The technical field relates to hand held mobile devices for ultraviolet light disinfection.

BACKGROUND

Ultraviolet (UV) light is an effective sterilization agent. The UV light breaks down living organisms to render them harmless.

SUMMARY

Convenient mobile sterilization devices are described herein that, in certain embodiments, provide secure storage in a niche in a protective housing and one-button action to automatically deploy and activate the device for quick and powerful destruction of germs on a surface using one hand. Users can hold the UV-light device and move it across a target surface to sterilize or disinfect the surface. The device may be compact, easily deployed, provided with a durable cover for secure storage, and equipped with safety shut-off features to prevent unwanted uses.

BRIEF DESCRIPTION OF THE FIGURES

FIG. 3A is a top view of the embodiment of FIG. 2;

FIG. 3B is a bottom view of the embodiment of FIG. 2;

FIG. 10C is a cross-sectional view of the embodiment of FIG. 10A taken along line C-C;

FIG. 10D is a cross-sectional view of the embodiment of FIG. 10A taken along line D-D;

FIG. 10E is a cross-sectional view of the embodiment of FIG. 10B taken along line E-E;

DETAILED DESCRIPTION OF PREFERRED EMBODIMENTS

Figure 1:
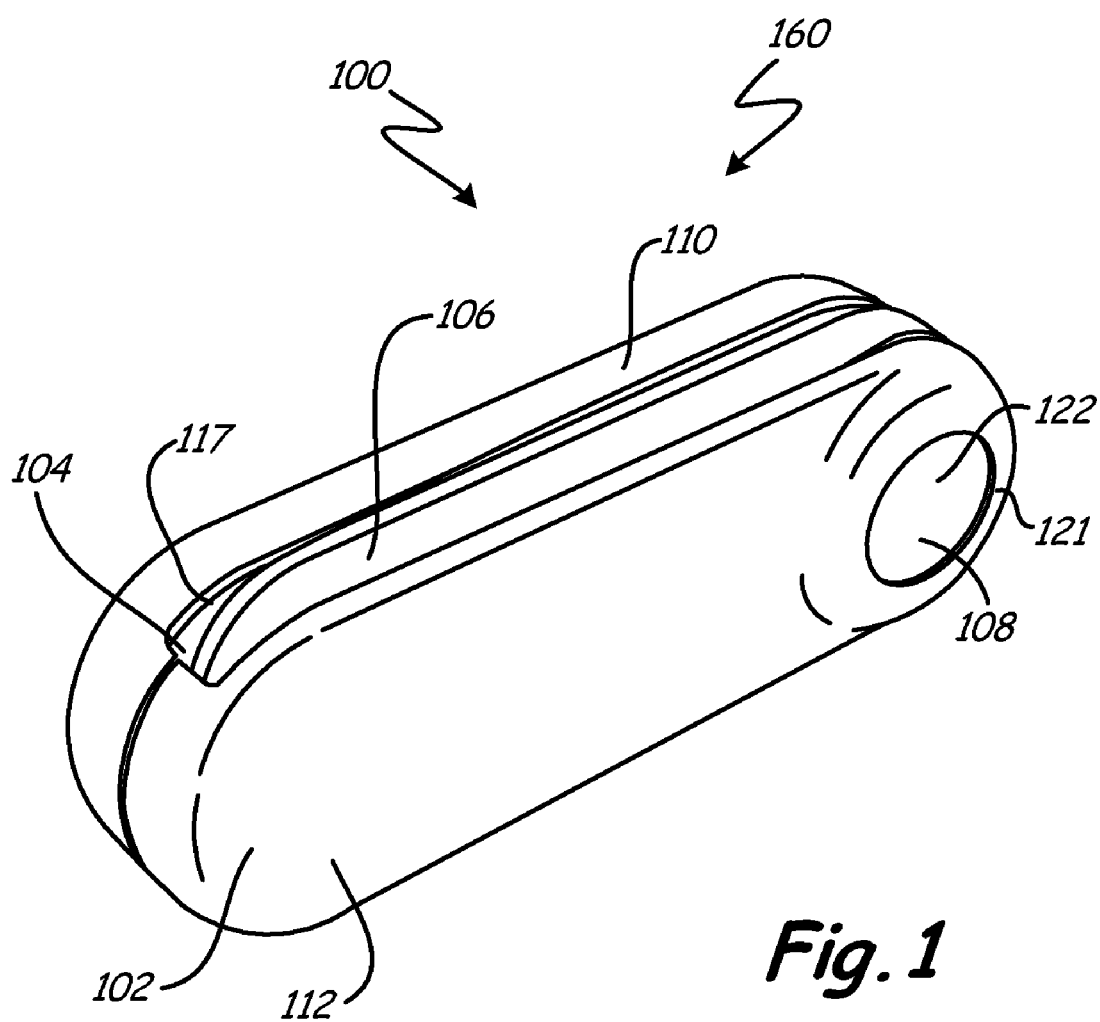
FIG. 1 is a perspective view of a hand-held sterilization device with a light housing in a niche in a storage position.
Figure 2:
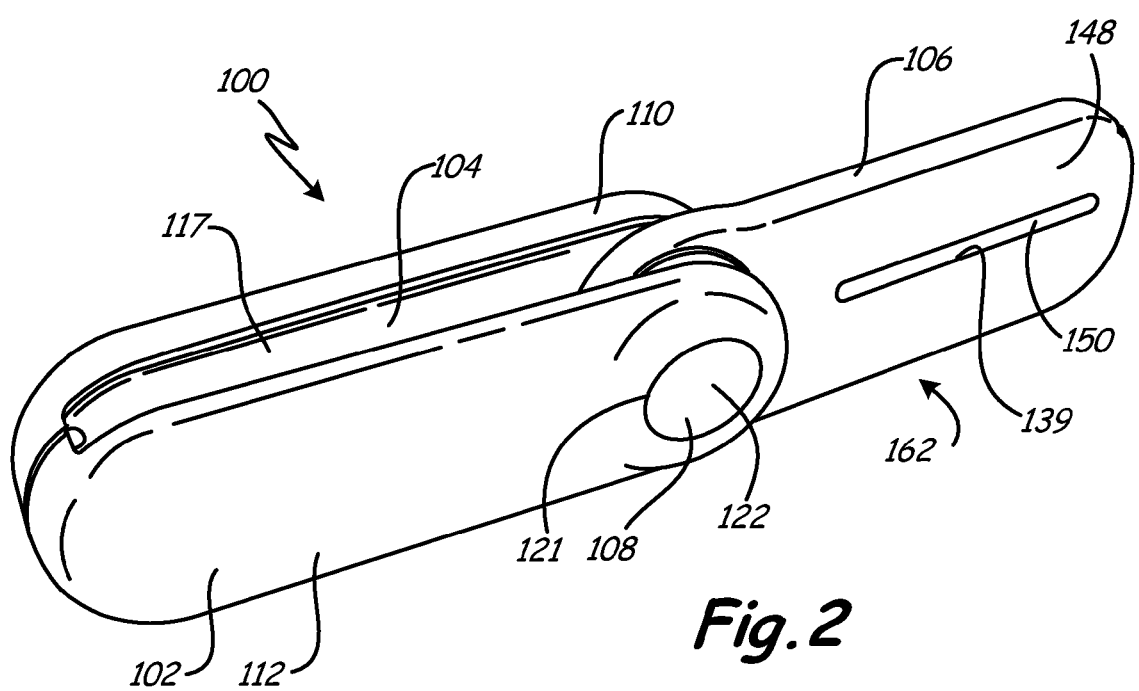
FIG. 2 is a perspective view of the embodiment of FIG. 1 with the light housing in a deployed position.
Figure 4A:
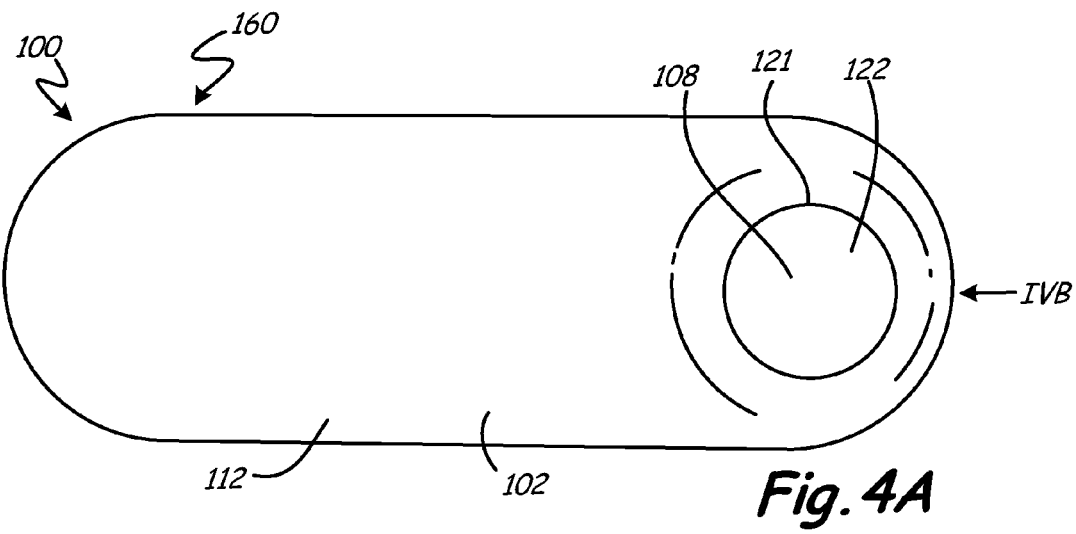
FIG. 4A is a top view of the embodiment of FIG. 1.
Figure 4C:
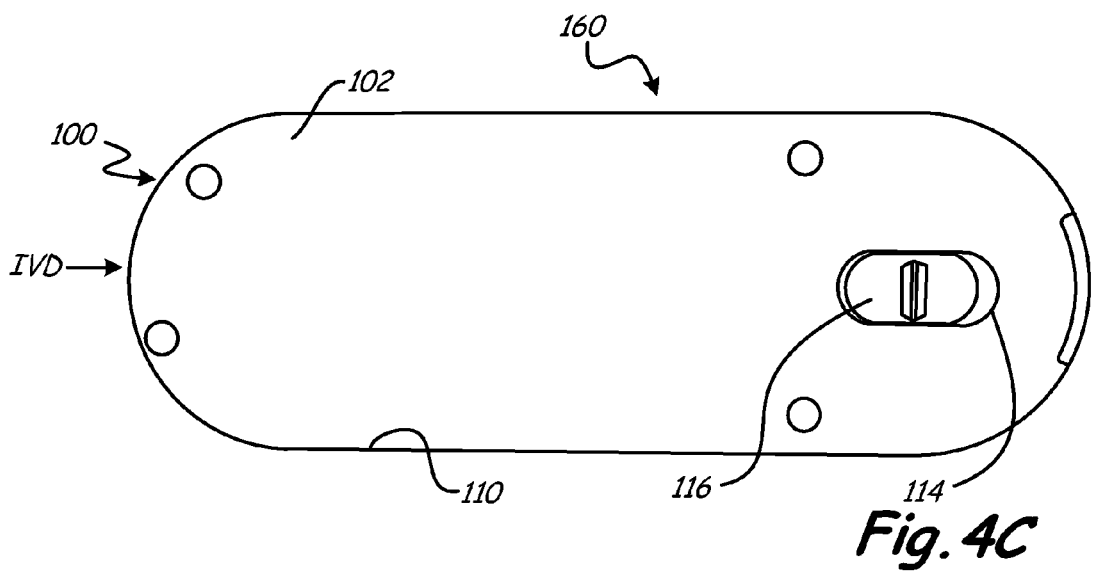
FIG. 4C is a bottom view of the embodiment of FIG. 1.
Figure 4B:
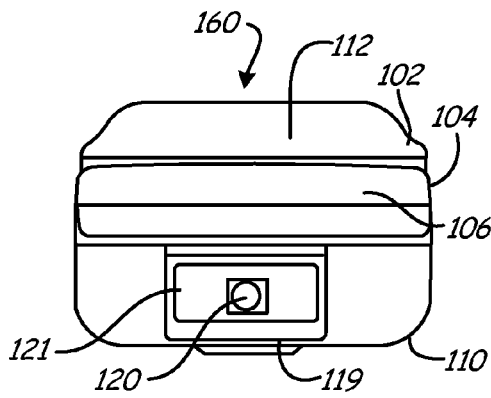
FIG. 4B is an elevated view taken along arrow IVB of FIG. 4A.
Figure 4D:
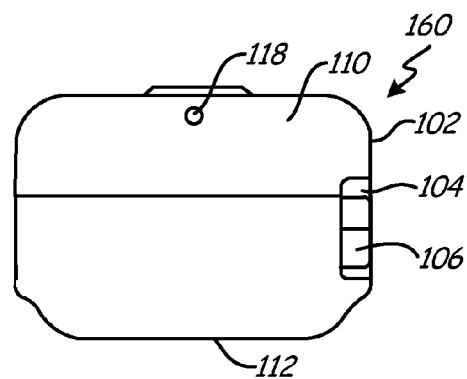
FIG. 4D is an elevated view taken along arrow IVD of FIG. 4A.

FIGS. 1-4 depict a hand-held sterilization device in a storage position with the light source covered. The sterilizer 100 has a covering housing 102 that receives a light housing 106 that are joined by rotating joint assembly 108, with light housing 106 being storable in niche 104. Covering housing 102 has subassemblies 110, 112. Subassembly 110 is a sub-housing with recess 114 to accommodate switch button 116, opening 118 for accessing a battery with a recharger (not shown), opening 119 for a flashlight assembly having a light bulb or light-emitting diode (LED) 119 and cover 120. Face 117 serves as a covering for the light source 142. Subassembly 112 has recessed area 121 to accommodate button 122 that actuates rotating joint assembly 108. Light housing 106 has recess 140 on light-emitting face 141 that accepts ultraviolet light source 142 that is mounted in sockets 144 that electrically communicate with a power source. Optional cover 146 protects light source 142. Recess 140 also has an opening 139 to allow light to pass to light-monitoring face 148 that has an opening with filter-covering 150 that allows light from the light source to pass through the filter to remove harmful wavelengths while allowing a user to visualize the on/off status of the light source.

In use, a user grasps device 100 in a hand, pushes button 122 to actuate rotating joint assembly 108 to automatically move light housing 106 from a covered (storage) position 160 to a deployed position 162 and also thereby turn on the light source to shine ultraviolet light from light source 142 through opening 143 in the light-emitting face 141. The housing 102 serves as a handle proximal to the user, with the light housing 106 being distal to the user. Device 100 has the light housing 106, light source 142, light-emitting face 141 all in a single plane along with the proximal portion and the covering face 117. The user moves the device to shine sterilizing light as desired on an object, and may monitor the on/off status of light source 142 by observing the presence or absence of light through filter 150 and opening 139. The device may turn itself off after a predetermined time via a processor (not shown). The user manually rotates light housing 106 back into niche 104 where it is retained and is automatically turned off. The light-emitting face 141 is parallel to face 117 in covered (storage) position 160 and deployed position 162. As depicted, this state of being parallel is maintained at all times, with face 117 being directly opposed to light emitting face 141 and light source 142 in covered position 160 and being parallel but not opposing the light emitting face 141 or light source 142 in deployed position 162. Parallel refers to a state of being within about 10 degrees of being absolutely parallel.

Figure 5:
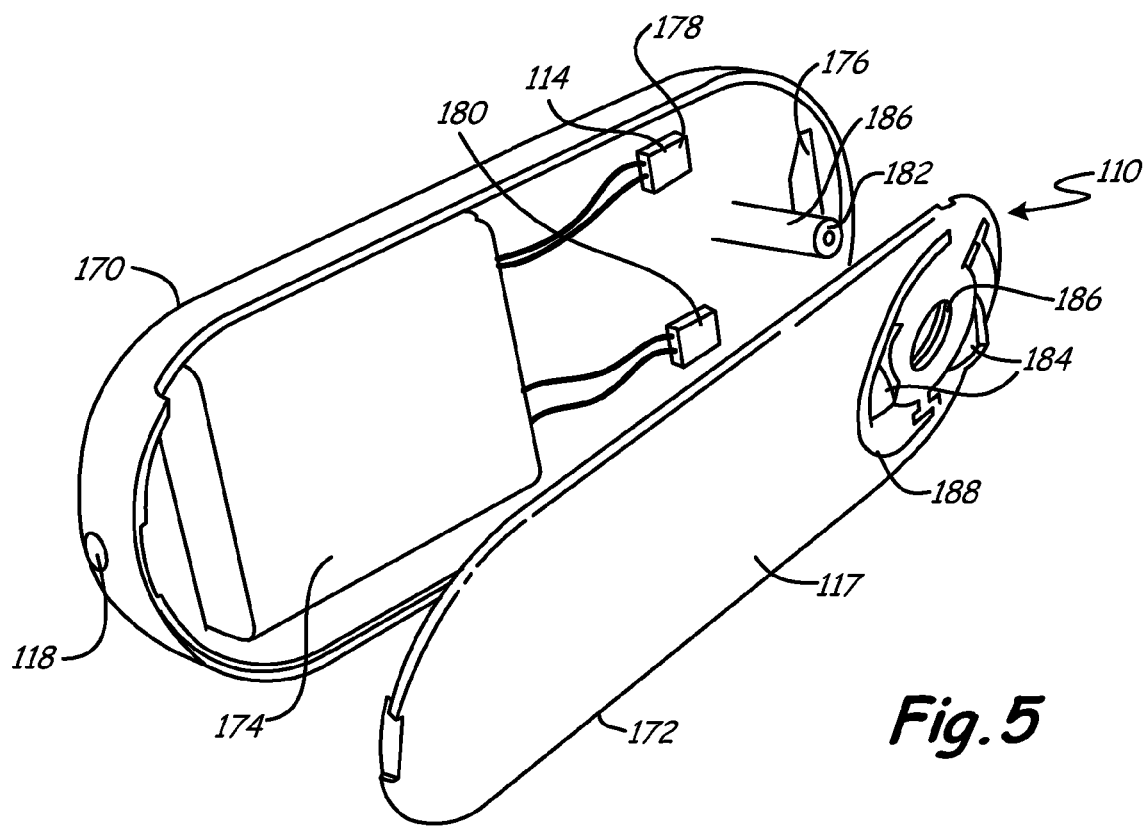
FIG. 5 is an exploded view of subassembly 110 of the embodiments of FIGS. 1-4.
Figure 6A:
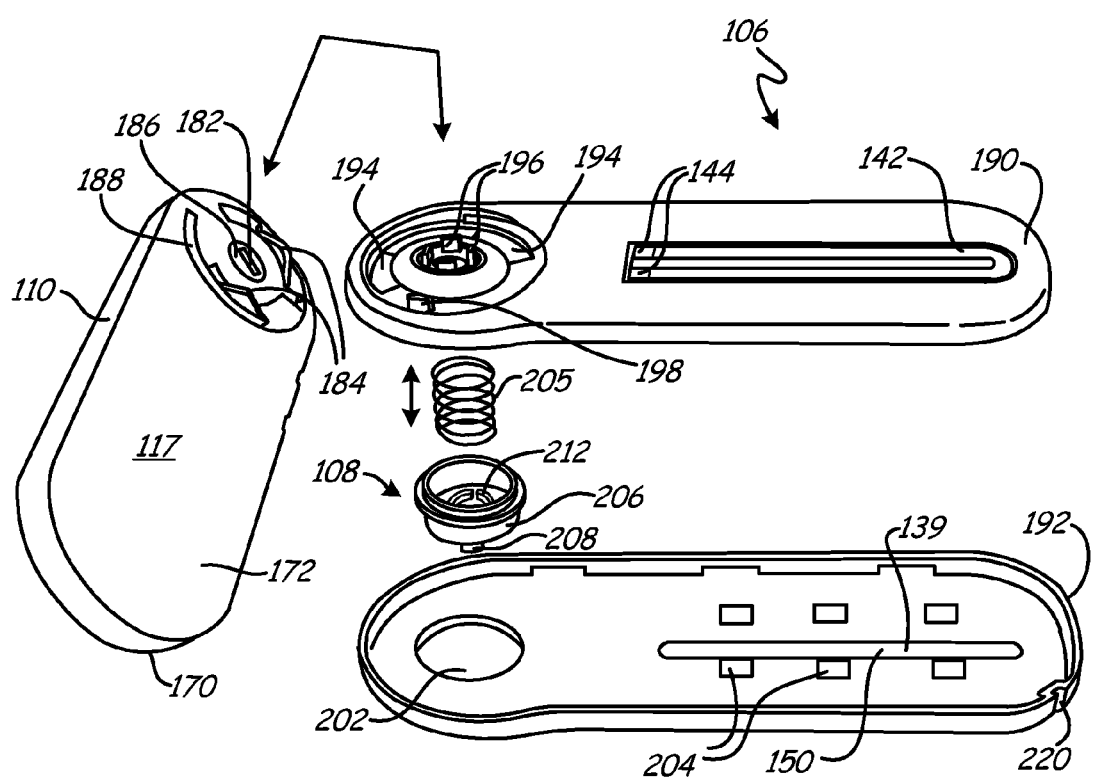
FIG. 6A is an exploded view of light housing 106 and rotating joint assembly 108 in relation to assembled subassembly 110 of the embodiments of FIGS. 1-4.
Figure 6B:
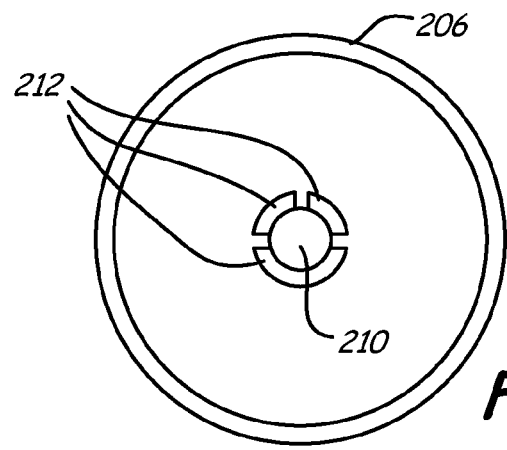
FIG. 6B is an enlarged bottom view of the rotating-biasing post depicted in FIG. 6A that forms part of the rotating joint assembly of the embodiments of FIGS. 1-4.
Figure 6C:
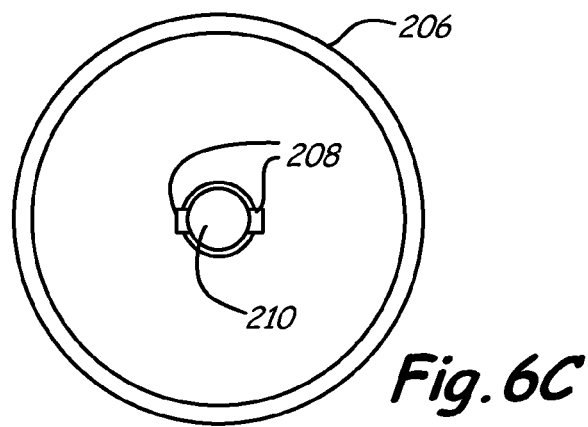
FIG. 6C is a top view of the embodiment of FIG. 6B.
Figure 6D:
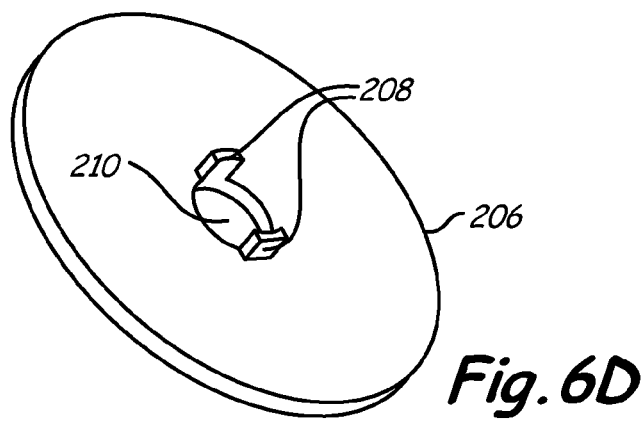
FIG. 6D is a perspective view of the embodiment of FIG. 6B.
Figure 7:
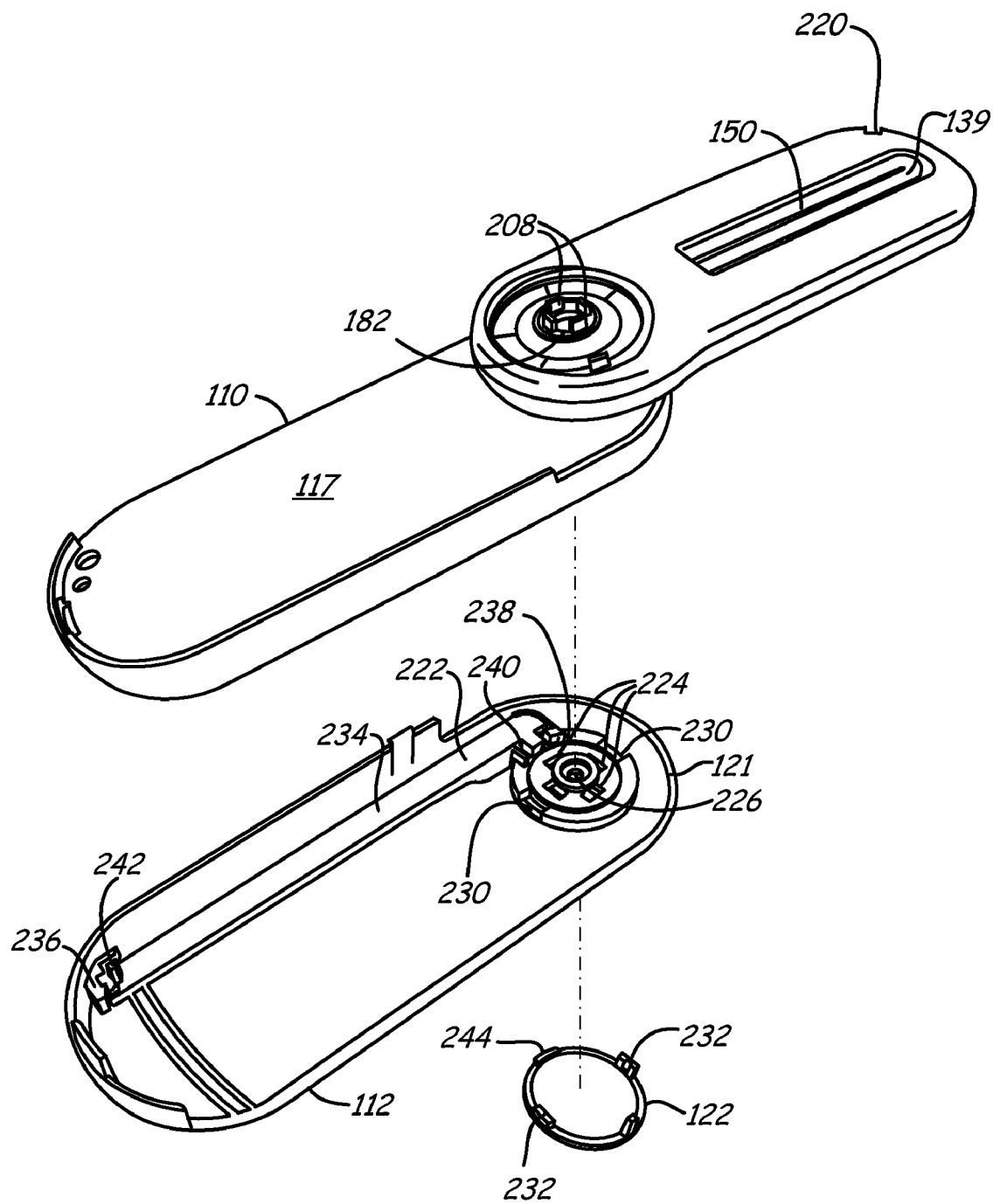
FIG. 7 is an exploded view of subassembly 112 in relation to subassemblies of FIGS. 5-6.
Figure 8A:
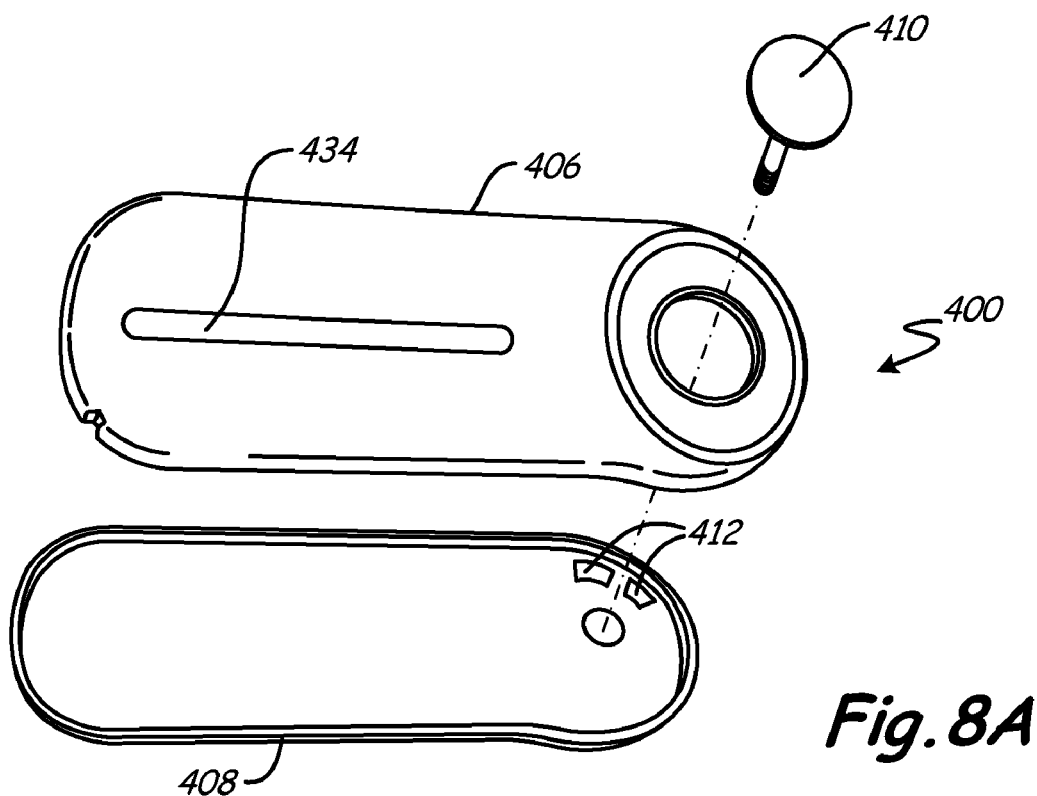
FIG. 8A is an exploded view of an alternative embodiment of a hand-held sterilization device with a rotating joint.
Figure 8B:
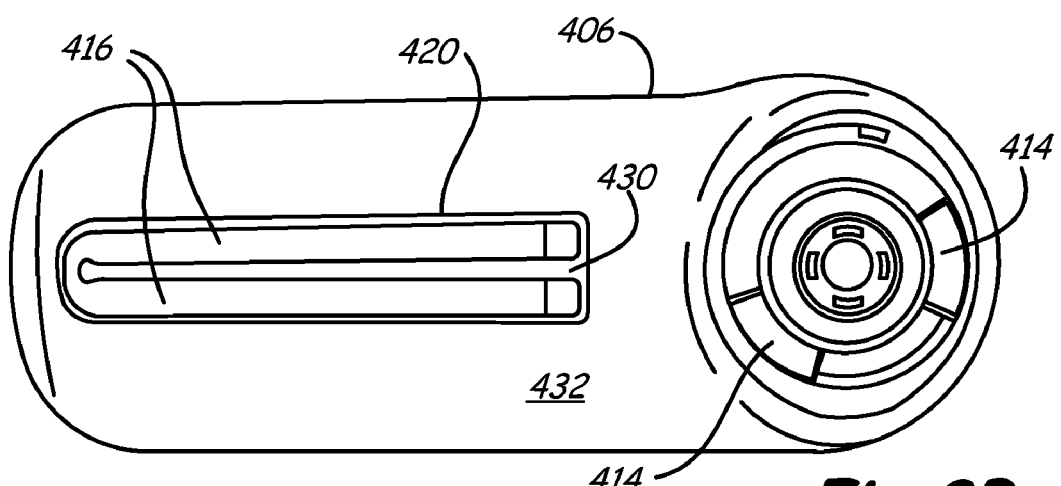
FIG. 8B is a bottom view of the light housing of the embodiment of FIG. 8A.
Figure 8C:
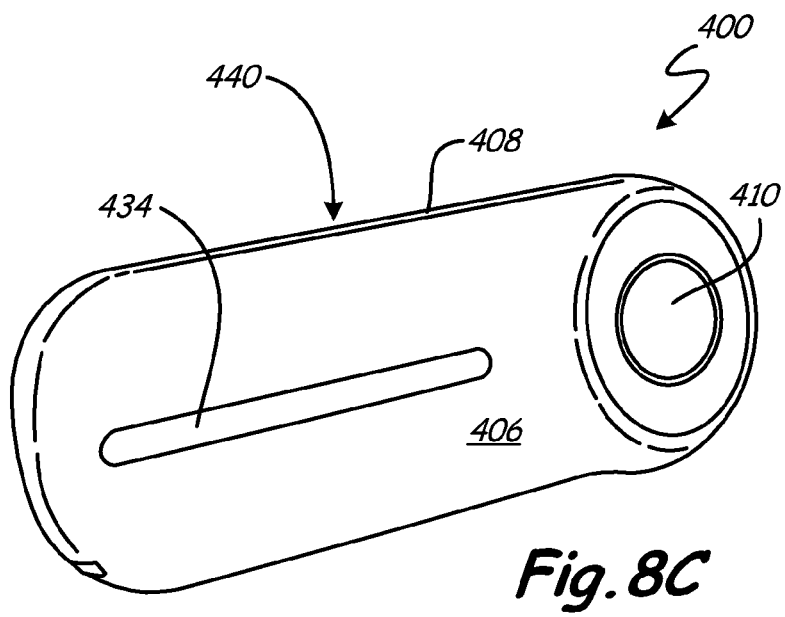
FIG. 8C is a perspective view of the embodiment of FIGS. 8A-8B with the light housing in a storage position.
Figure 8D:
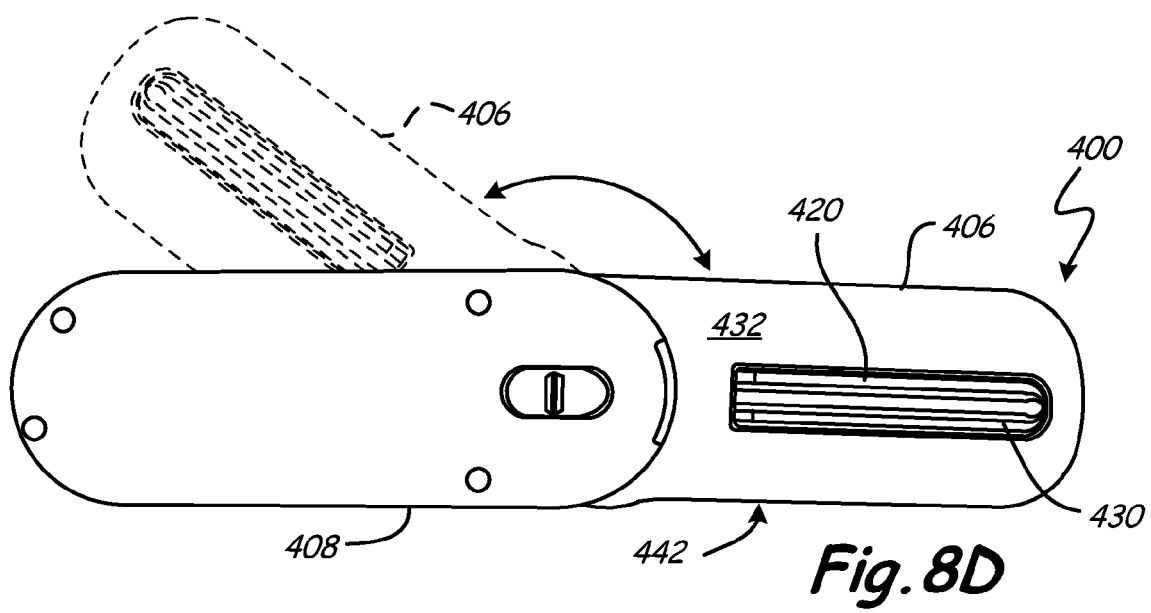
FIG. 8D is a perspective view showing rotation of the light housing for the embodiment of FIGS. 8A-8C.

FIGS. 5-7 depict the embodiment of FIGS. 1-4 in further detail. FIG. 5 depicts subassembly 110, which has base housing 170 and fitted top 172. Housing 170 contains battery 174, lamp or LED assembly 176 connected to battery 174 via switch 178 that is switchable by switch button 116. The housing 170 also contains attitude sensor 180, a post 182, and electronic components as needed for operation of the device (not shown). A microprocessor (not shown) may also be included in housing 170. Fitted top 172 has flexible upwardly biased battery connector contacts 184, post opening 186, and arcuate guide slot 188. A rechargeable battery rechargeable through power source connectable at opening 118 is depicted but any suitable power source may be used, e.g., disposable batteries. Battery contacts 184 are connected to battery 174 via attitude sensor 180. The attitude sensor allows current to pass when the sensor is disposed within a predetermined range, or, alternatively, blocks current when disposed outside of a predetermined range. Top 172 fits onto housing 170, e.g., with interlocking tabs and/or screws, with post 182 passing through post opening 186.

FIG. 6A depicts subassembly 110 as assembled and light housing assembly 106 disassembled into first shell 190 and second shell 192. First shell has battery connector contacts 194, mounting posts 196, guide post 198, and ultraviolet light source 142 electrically connected to contacts 194. Second shell 192 has opening 139 with cover 150, opening 202, and tabs 204. Rotating joint assembly 108 includes spring 205, rotating-biasing post 206 with ears 208 about axial bore 210, and tabs 212, see also FIGS. 6B-6D. Spring 205 has a first end disposed between tabs 212 to prevent slippage of the spring end, and the other end of spring 205 is placed in tabs (not shown) in shell 190 that prevents slippage of the spring end. The post 206 is fit into opening 202 with ears 208 projecting therethrough. Tabs 204 cooperate with corresponding mounts (not shown) on shell 190 as shells 190 and 192 are joined to make light housing assembly 106. Assembly 106 is mounted on subassembly 110 with post 182 passing through bore 210 of rotating-biasing post 206 with tabs 196 fitting into post opening 186, while guide post 198 fits into arcuate guide slot 188. Battery contacts 184, 194 are not opposing or contacting each other with the light housing 106 in niche 104, but move to contact each other as housing 106 is rotated into deployment position 162. Light housing assembly 106 has slot 220 for restraining the housing from rotation by cooperation with a post engaging the slot.

FIG. 7 depicts light housing assembly 106 as assembled and engaged on subassembly 110. Subassembly 112 has recessed area 121 and sliding bar assembly 222. Recessed area 121 has slots 224 for engaging ears 208 and bore 226. Slots 230 accept tabs 232 of button 122 when assembled. Sliding bar assembly 222 has bar 234 attached to biasing spring 236, tapered post 238 facing hole 240, and restraining post 242. Subassembly 112 is joined to subassembly 110 with fasteners, e.g., adhesives, interlocking tabs or screws, with ears 208 passing into a set of slots 224. Button 122 tabs are snapped into slots 230 to secure the button while allowing up and down movement. Button post 244 is placed in or over hole 240 and at or near tapered post 238. The light housing may be pushed into niche 104, which winds spring 205; restraining post 242 engages slot 220, with spring 236 biasing bar 234 to prevent movement of post 242. User depression of button 122 forces button post 244 against tapered post 238 and forces bar 234 out of slot 220 to release the restraint on spring 205. Spring 205 then unwinds, rotating light housing assembly 106 into the deployed position. For additional force, spring 205 may be further wound during assembly.

FIG. 8 shows an alternative embodiment 400, with light housing 406 and base housing 408 secured by threaded fastener 410. Other fasteners may be used that provide for relative movement of housings 406 and 408. Base 408 has an internal battery source that provides power to battery connectors 412. Light housing 406 has battery connectors 414 and light sources 416 electrically connected to the connectors. The light sources are located in a recess 420. Light sources 420 can emit light through opening 430 located in light-emitting facing 432 and also through optional viewport 434 having a suitable filter in the case of ultraviolet light or an otherwise translucent covering. In use, a user rotates light source housing 406 in a plane parallel to a plane defined by light-emitting facing 432, moving from a storage position 440 wherein the light source is covered and a deployment position wherein the battery connectors 412, 414 are aligned to pass electricity to the light source to turn on the light source and emit light. In the case of an ultraviolet light source, a user may illuminate an object that is to be sterilized. While electronic components and batteries are generally depicted as being separate from the light emitting source, some or all of such components may be put into the same housing as the light source. Accordingly, a simple cover free of electronic components may be used to cover the light source as desired, with the cover being rotated in the plane as described or pulled out as described elsewhere herein. Quick-deployment embodiments may include a biasing member that forces the light housing away from the base, e.g., a spring restrained until a button is actuated by the user.

Figure 9B:
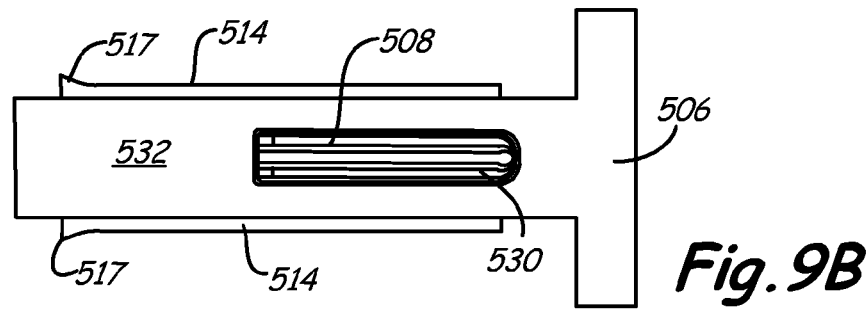
FIG. 9B is a bottom view of the light housing of FIG. 9A.
Figure 9A:
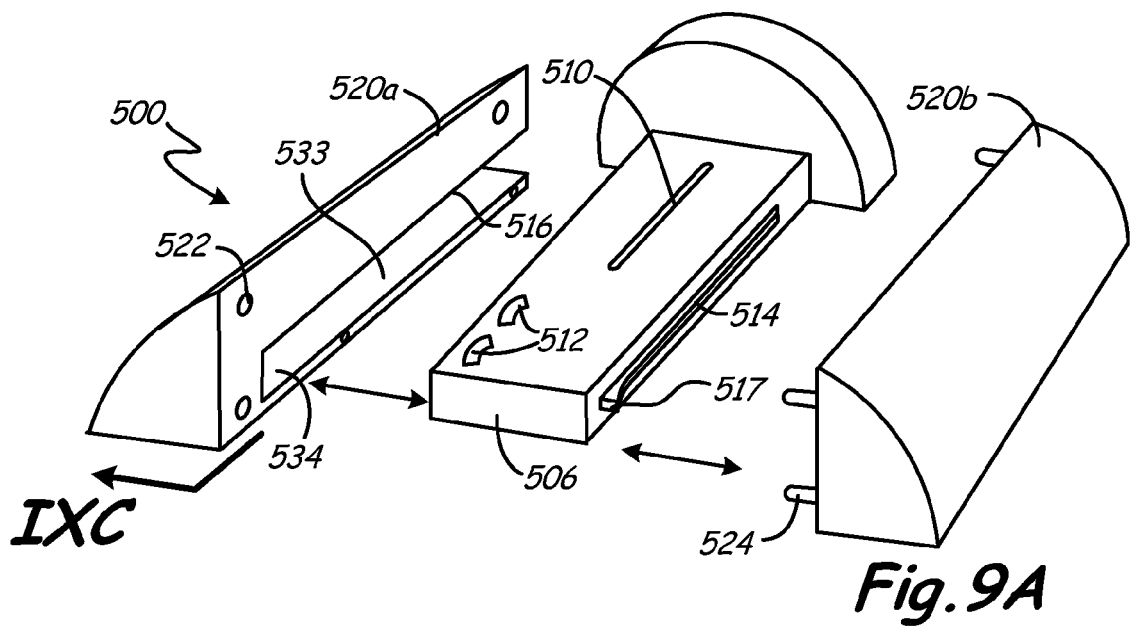
FIG. 9A is an exploded view of an alternative embodiment of a hand-held light-emitting device using linear motion for movement of a light source from a storage position to a deployed position.
Figure 9C:
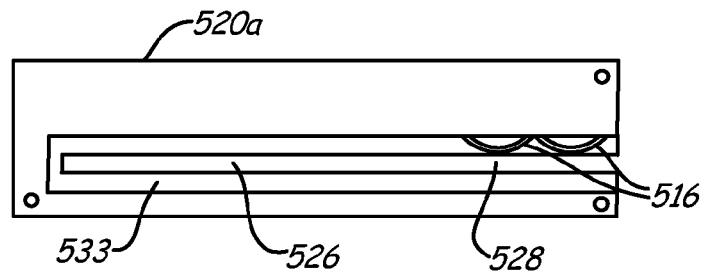
FIG. 9C is a view along the arrow IXC of FIG. 9A.

FIG. 9 depicts an alternative embodiment 500 of a hand-held sterilization device. A light housing 506 has a light source 508, optional light source viewing port 510, contacts 512, and guide bars 514. The housing 506 has an internal battery (not shown) and components to establish an electrical connection to light source 508 through contacts 512, which must contact contacts 516 for the circuit to be complete, with completion of the circuit causing the light source to be turned on. Bars 514 have posts 517 to prevent the housing 506 from being pulled out of the outer housing 520. The light source housing 506 is received by outer housing 520 made of subassemblies 520a and 520b, which are equipped with suitable fasteners to join them together, e.g., mortise and tenons 522, 524. FIG. 9C depicts subassembly 520a having guide slot 526 that cooperates with bar 514 to guide housing 506 in and out of the outer housing 520. Guide slot 526 has a stop 528 to catch posts 517. The light source 508 is disposed in a recess 530 in light-emitting face 532. The outer housing has covering face 534 formed by assemblies 520a, 520b to make a cover that is parallel to covering face 534, with the covering face being both parallel to and opposite of (and covering) the light source when it is in a storage position. The outer housing forms a niche 533 to contain the light housing in the storage position. The covering face 534 is parallel to the light-emitting face 532 in the deployment position wherein the light source housing is pulled forward. In use, a user, pulls the light source housing from the outer housing to engage contacts 512 with contacts 516 to thereby turn on the power source. Alternatively, a biasing mechanism, (e.g., a spring, not shown) may be placed behind housing 506 to force the light housing out of the outer housing and turn on the light source by completion of the circuit through contacts 512, 516; in this embodiment, a button for example, may be used to release the light housing.

Figure 10A:
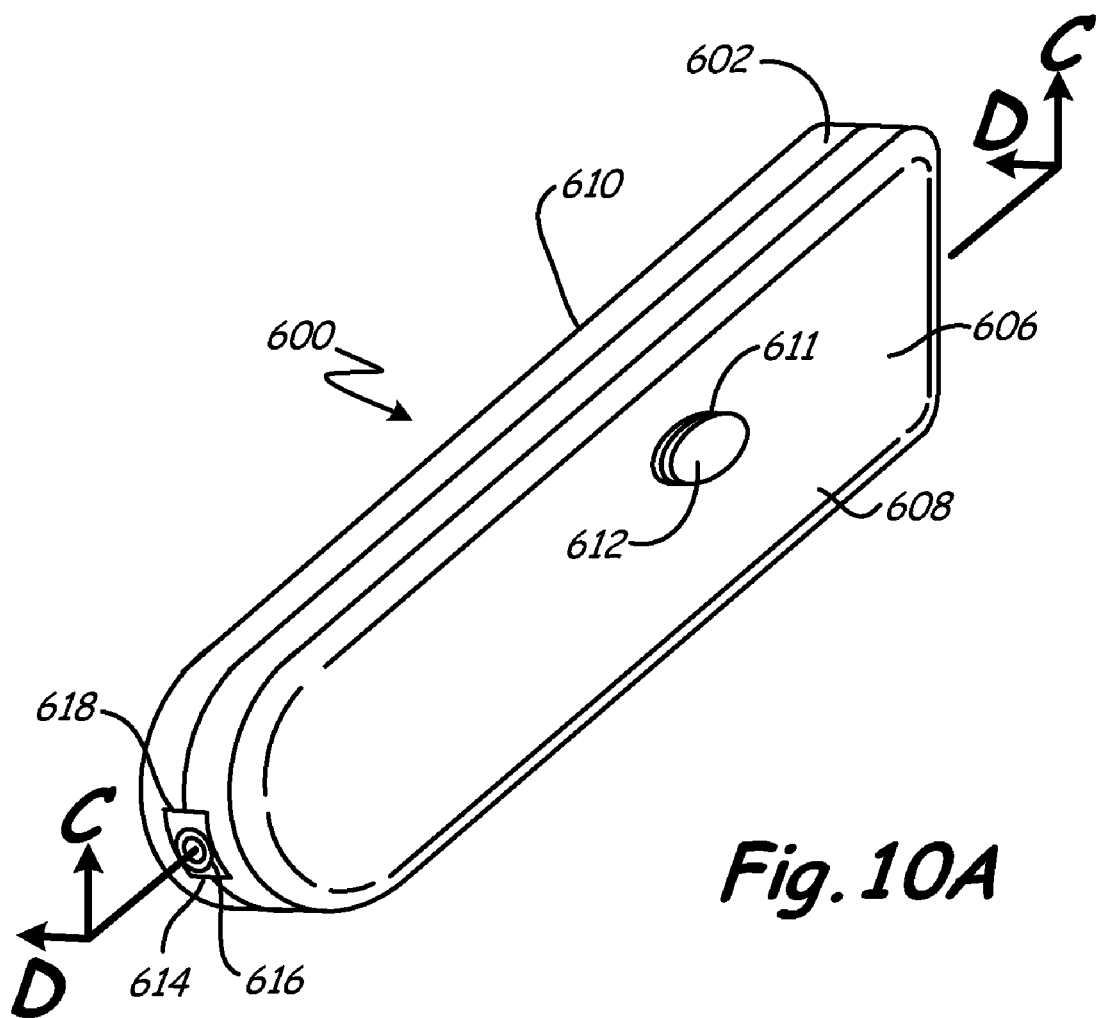
FIG. 10A is a perspective view of an alternative embodiment of a hand-held light-emitting device in a retracted position using linear motion for movement of a light source from a storage position to a deployed position.
Figure 10B:
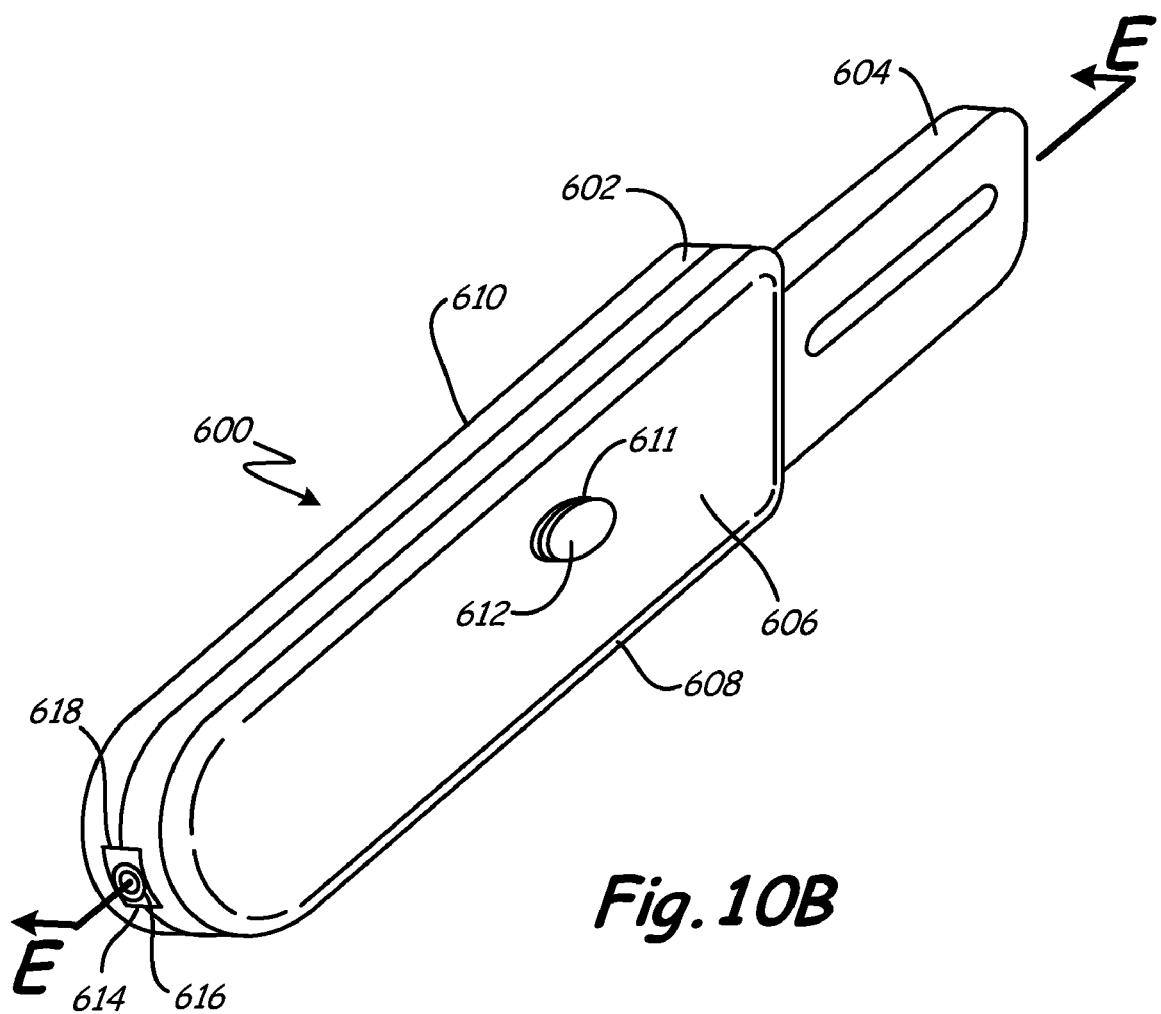
FIG. 10B is a perspective view of the embodiment of FIG. 10A with the light emitting device being in the extended position.

FIG. 10 depicts an alternative embodiment of a system using a biasing mechanism to force a light source from an outer housing. Device 600 has outer housing 602 that has light housing 604 and outer housing 606. Outer housing 606 has subassemblies 608 and 610 joined together. Subassembly 608 has opening 611 for receiving button 612. Recesses 614, 616 cooperate to form an opening for access to charger receptacle 618. Subassembly 610 has cavity 620 to receive light housing 604, spring 621, recesses 622 for contacts 626, with cavity 620 also receiving battery pack 628. Button assembly 640 has button 612, biasing member 642, pivot 644, and tab 646; in use, a user presses button 612 to force it downwards to move tab 646 outwards to thereby release the light housing 604 from outer housing 606 by action of spring 621. Light housing 604 has recess 650 with light source 652 electrically connected to contacts 654, with light from light source 652 being emitted from the recess 650 when the light is turned on by completing a circuit by contact of contacts 654 and 622, with contacts 622 being in electrical connection to rechargeable battery 628. Shoulders 656 of light housing 604 are stopped by shoulders 658 to prevent the light housing from being overextended relative to outer housing 602. Spring 621 is anchored to outer housing 602 and seats inside the light housing 604 in recess 660. A user may deploy the light housing 604 by pressing button 612 as described to allow the light housing 604 to be forced out of the outer housing 602. Deployment of the light housing 604 allows completion of the light-to-battery circuits to turn on the light source 652. The user may force the light housing 604 back into the outer housing 602 to reset the button assembly 640 to retain the light housing. Other features described herein may also be included in this embodiment.

As depicted in FIG. 10, the outer housing provides a covering for the light source when it is in the retracted storage position. The movement of the light housing is in a single direction and along a single axis, e.g., the central longitudinal axis of the light source or light source housing.

Figure 11A:
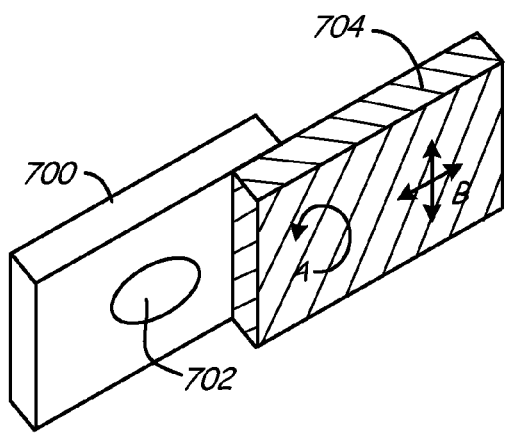
FIG. 11A is a conceptual perspective view of a light source housing and a covering housing, with parallel movement being indicated.
Figure 11B:
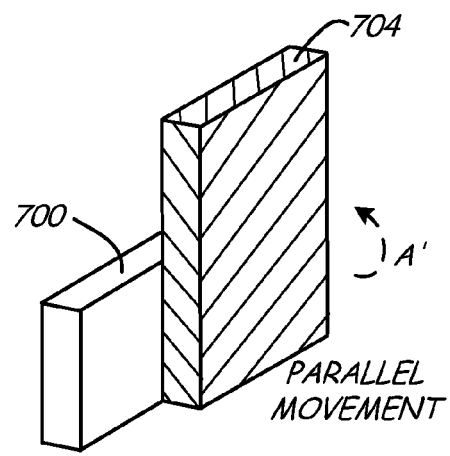
FIG. 11B shows the housing and cover of FIG. 11A as rotatedly moved parallel to each other.
Figure 11C:
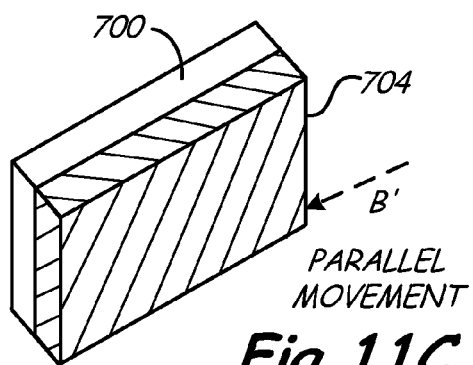
FIG. 11C shows the housing and cover of FIG. 11A as linearly moved parallel to each other.
Figure 11D:
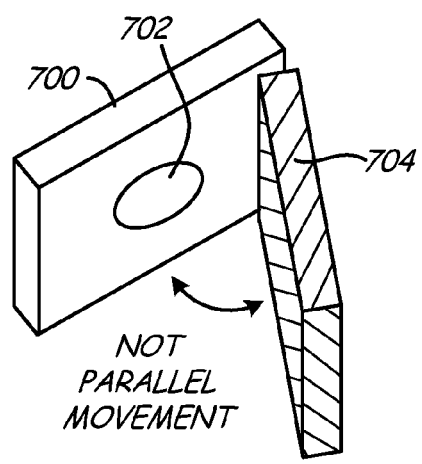
FIG. 11D shows the housing and cover of FIG. 11A in a movement that is not parallel relative to each other.

Accordingly, certain embodiments relate to moving a light source and/or light source housing from a storage position wherein the light source is covered to a deployed position wherein light from the light source can be emitted to an intended surface. The movement may be made with the light source housing being held parallel to the covering. The movement may be, e.g., a rotating movement in a single plane or a linear movement without rotation in a single plane. FIG. 11 depicts linear or rotating movement of a light housing and a covering parallel to each other and also depicts non-parallel movement by way of contrast. FIG. 11A depicts light source housing 700 with light source 702 and covering 704 arrows A and B indicating parallel movement of the covering and light source housing relative to each other. FIG. 11B shows covering 704 after a rotating movement parallel to housing 702 as indicated by dashed arrow A', with the covering being in a covering position. FIG. 11C shows covering 704 after a linear movement parallel to housing 702 as indicated by dashed arrow B', with the covering in a covering position. FIG. 11D shows the covering 704 in a rotating movement that is not parallel to the light housing 702

Movement in a single plane allows for attitude sensors to be effectively incorporated into the device since the device can be made with a proximal portion easily grasped by a user and a distal light-housing portion that is in substantially the same plane, so the attitude of the device in use is readily controlled. In contrast, devices made with a bend between the light source and a handle area have an uncertain geometry during use, with the user having to adjust a hand position to compensate for the light source and handle being in different planes.

Also, certain embodiments provide a niche for secure and durable storage of the light housing with the niche providing protection of all of, or a substantial portion of, the light housing. Further, certain embodiments require electrical contacts to be completed for the light source to be activated or to remain on. This arrangement is more secure than relying on a separate switch that controls the light in response to a covering being open or closed. Moreover, the contacts may be used to transmit power from a power source to the light housing instead of interconnected wiring that has to be threaded from the power source to the light source. Certain embodiments provide for secure single-handed operation, with a single button actuating the light housing to move from a storage position to a deployed position and to also activate the light source.

Various attitude sensors may be used to provide safety on/off controls. An accelerometer or accelerometers may be used, for instance. An xyz accelerometer may be used to provide an object's attitude, i.e., its coordinates in an xyz coordinate system. In the case of a known device geometry, all the points on the object can be mapped into the xyz coordinate position with a single xyz accelerometer. Alternatively, separate devices can provide inputs that in combination describe an object's attitude, for instance an xy accelerometer and a tilt indicator for the z-position. Accelerometers may be used in combination with a microprocessor, for instance an xy or an xyz accelerometer. Some embodiments use a tilt detector to determine an attitude of the device. Accordingly, some embodiments include an xy accelerometer and a tilt detector, and other embodiments may also include a tilt detector. An embodiment of a tilt detector is an electronic inclinometer, e.g., of a type in the group accelerometer, liquid capacitive, electrolytic, gas bubble in liquid, pendulum, and MEMS (Micro-Electro-Mechanical Systems).

In some embodiments, the light source or device is unpowered when an attitude sensor is more than a predetermined value from vertical, with the value being in a range from, e.g., about 5 to about 180 degrees; in other words, the light is on if it points vertically down at the surface but is turned off when it deviates too much, e.g., is rotated 90 degrees away; artisans will immediately appreciate that all the ranges and values within the explicitly stated ranges are contemplated, e.g., about 15, about 45, about 90, or between about 45 degrees and about 90 degrees. A ball in a swivel socket, for instance, may be used, with the position of the ball relative to its socket controlling a flow of current to a light source.

Some embodiments use an attitude sensor to prevent the light source from being on when the light source deviates by more than a predetermined angle. For instance, when the light-emitting face of the device is parallel to a horizontal surface, the angle may be between e.g., 15 and 90 degrees; artisans will immediately appreciate that all the ranges and values within the explicitly stated ranges are contemplated. One such angle may be the reverse angle and another is the angle from vertical. The reverse angle is the angle traced by the edges of the device when it is in the deployed position horizontal to the ground to emit light towards the ground and rotated about a central axis passing through the length of the device, as in a user twisting a wrist to make the light source move from horizontal to pointing sideways. The vertical angle is made by the device when it is in the deployed position horizontal to the ground to emit light toward the ground and the device is moved so that its a central axis passing through the length of the device is perpendicular to the ground, as in a user bending an arm from a straight horizontal position until the elbow forms a 90 degree angle with the hand uppermost.

Hand-held is a term referring to a device for a user to hold and support the entire device in a hand and move across a target surface. Embodiments of hand-held devices include those with a weight of less than about 5 lbs, less than about 1 lb and less than about 8 ounces; artisans will immediately appreciate that all the ranges and values within the explicitly stated ranges are contemplated. A switch or a button that is actuated by a user is a broad term and may include, for example, a toggle, a sliding switch that allows adjustable control of the component being switched, hand-actuation, knobs, rheostats, and wheels (e.g., thumbwheel). Batteries may be disposable or rechargeable, e.g., by electric current or solar cells. A power cord and plug may be used to augment or substitute for battery-operation.

Microprocessors may be used as needed to achieve the indicated functions. In general, a microprocessor refers to one or more computing devices that compute using hardware, software or firmware. A single microprocessor may be used in many embodiments, or a plurality of microprocessors may share computing tasks. The microprocessor may contain, or cooperate with, a computer-readable medium that provides computer-readable instructions, data, and electronic records. The term computing device is broad and includes microprocessors and integrated circuits that perform logical computing operations.

The light source may be an ultraviolet light (UV) source, e.g., ultraviolet A (UVA; about 400 nm to about 315 nm), ultraviolet B (UVB; about 315 nm to about 290 nm), and/or ultraviolet C (UVC; about 290 nm to about 100 nm). UVC can be found in artificial sources such as mercury arc lamps and germicidal lamps. Light sources commonly referred to as UVC lamps can be used. Some light sources are referred to as high pressure UVC lamps, and typically have a peak at about 254 nm and a secondary peak at about 185 nm. Medium pressure UVC lamps vary somewhat and typically have multiple peaks from abort 225 nm to about 600 nm. Alternatively, visible light sources (bulbs or light emitting diodes) may be substituted for sterilizing light and the device may be used as a flashlight or pocket reader instead of a sterilizing device.

Table 1 details some dosages for sterilization. The cleaning mechanism of UV is a photochemical process. The indicated organisms or other compounds undergo breakdown when exposed to high intensity UV at about 240 to 290 nm. Shortwave ultraviolet light can destroy DNA in living microorganisms and breakdown organic material found in indoor air. UVC's effectiveness is directly related to intensity and exposure time. UV rays strike contaminants directly to penetrate it and break down its molecular bonds. This bond breakage translates into cellular or genetic damage.

Some embodiments accordingly relate to exposing a target area to a light source to sterilize the area for a particular condition or organism causing the condition until the target area is exposed to at least a dose of light that sterilizes the surface, meaning a 99.9% kill rate as measured under controlled conditions. Other embodiments relate to sanitizing a surface target area, meaning that the area is exposed to a dosage of light calculated to remove unwanted compounds without fully sterilizing the surface, e.g., about 25% to about 98%; artisans will immediately appreciate that all the ranges and values within the explicitly stated ranges are contemplated, e.g., from about 50% to about 80%. Certain embodiments of sanitization/sterilization are directed to one or more combinations of organisms or conditions and/or specific items and/or areas and/or area sizes and/or light source devices as in Table 1. The data of Table 1 has been made based on tests of prototypes. Disinfecting is a term applied to either sanitization or sterilization. Certain methods of use include shining a UV light at an object for a predetermined amount of time as indicated in Table 1, and/or selecting an object from Table 1 for exposure as indicated. The prototype was made with a UVC output of about 1.5 Watts to provide an intensity of about 5000 microwatts per square centimeter and about 30,000 microwatts total UV light output. Alternatives include a device with more or less output, e.g., from about 1 Watt to about 40 Watts, from about 2000 to about 50,000 microwatts per square centimeters, and from about 5,000 to about 300,000 microwatts total UV output; artisans will immediately appreciate that all the ranges and values within the explicitly stated ranges are contemplated, e.g., 36 Watts, 5-20 Watts. In the case of the relatively higher-powered units (or any of the units), weight may be conserved by using external power (e.g., to a 110 volt power outlet) as opposed to a battery.

In general, the device may be provided with instructions that outline usage guidelines, for instance the how long to expose an area to achieve various levels of sanitization for a variety of organisms. In one method, the user is instructed to provide a series of passes over the intended target area. Embodiments include a kit that has a hand held sterilizing device and instructions for using the device as described herein.

As is evident from the foregoing, one embodiment is a hand-held device for sanitizing and/or sterilizing a surface comprising a hand-held light source housing comprising an ultraviolet light source in a receptacle in the housing, with a light-emitting face of the housing having an opening for emitting light from the light source; a covering housing rotatably mounted to the light source housing, with the covering housing having a niche for receiving the light source housing and comprising a covering face parallel to the light-emitting face of the housing; wherein the light source in the light source housing is rotatable from a covered position inside the niche with the opening being covered by the covering housing to a deployment position outside the niche with the opening not being covered by the covering housing, with the covering face and the light-emitting face being parallel as the covering housing is rotated out of the niche to the deployment position.

Such devices may have contacts for completing a circuit between a power source (for instance a battery or power cord) and the light source, with the contacts being safety features that only provide power to the light source when it is properly moved into the deployed position. The device may be made wherein the covering housing comprises a battery and a first set of contacts and the light source housing comprises second set of contacts that contact each other upon the rotation to the deployment position to complete an electrical connection through the contacts between the battery and the light source to power the light source in the deployment position but not in the covering position.

Such devices may be configured with attitude sensors. For instance, a device may comprise an attitude sensor in a circuit for turning off the light source when the light source exceeds a predetermined angle. The sensor may be, or comprise, a swivel ball, tilt sensor, or an accelerometer. The predetermined angle may be 90 degrees from a horizontal position or a vertical position.

Such devices may include a biasing mechanism to force the device from a storage to a deployed position. For instance, the device may be spring-loaded. Some embodiments are comprising a spring that biases the light source housing to move from the covered position to the deployment position. The biasing force may be restrained as needed, e.g., with a tab that restrains the light source housing in the covered position until a user depresses a button that causes the tab to move and thereby allows the spring to move the light source housing from the covered position to the deployment position.

The device may further comprise a second light source, e.g., a bulb or an LED actuated by a switch to provide visible light on demand.

An embodiment of the device is a light housing with a cover that moves off the light source while staying parallel to the light housing, with the plane defined by movement of the cover being parallel to the plane defined by the opening in the light housing. The movement can be viewed as the cover moving and the light housing staying still, or vice versa, or with both moving. One embodiment is a device for sanitizing a surface comprising a light source housing comprising a receptacle for a light source comprising a socket for the light source, with a light-emitting face of the housing having an opening for emitting light from the light source; a covering rotatably mounted to the light source housing, with the covering having a covering face parallel to the light-emitting face of the housing; wherein the light source housing is rotatable from a covered position with the opening being covered by the cover to a deployment position with the opening not being covered by the cover, with the covering face and the light-emitting face being parallel as the light source housing is rotated.

A method by a user of sanitizing an object may be comprising moving a light source in a light source housing from a niche inside a covering housing to a deployed position to thereby uncover the light source and to activate the light source to emit ultraviolet light from the light source housing onto the object that a user intends to sanitize, and moving the device by hand to emit the light onto the object and thereby kill organisms on the object to sanitize the object, with the light source being recessed in a light-emitting face of the light source housing and the covering housing comprising a covering face that is parallel to and opposed to the light-emitting face in the covering position and that is parallel to the light emitting face in the deployed position. The light-emitting face and the covering face may be parallel to each other as the light source housing is rotated from the niche to the deployment position. The light-emitting face and the covering face may be parallel to each other as the light source housing is slid out from the niche to the deployment position. The sliding motion may be linear.

In certain embodiments, a hand-held device for sanitizing a surface is provided comprising a hand-held light source housing comprising an ultraviolet light source in a receptacle in the housing, with a light-emitting face of the housing having an opening for emitting light from the light source; a covering housing receiving and covering all or a portion of the light source housing and/or the light source; wherein the light source housing being movable from a covered position inside the niche (with an opening for the light source being covered by the covering housing) to a deployment position outside the niche (with the opening not being covered by the covering housing), with the covering and the light housing being parallel as the covering housing is moved linearly out of covering housing to the deployment position. The movement may be initiated by pressing, e.g., a button, which is a broad term encompassing a trigger or tab or user-actuated deployment structure. In some embodiments, the button is part of a button assembly, with the button (optionally pivotally) moving a tab that restrains the lighting housing, which housing is biased to move out of the outer housing by a biasing structure, e.g., a spring or coil. The lighting housing may have a recess to receive the tab to thereby be restrained. The lighting housing may further comprise a bore that receives some or all of the biasing member, e.g., for storage of substantially all of the biasing member when the lighting housing is in the covered storage position.

The user may operate the device for a predetermined time, including the times and for the conditions as indicated in Table 1. Certain embodiments are directed to kits that comprise a device and instructions for the device. The instructions may comprise one or more of the times and conditions as indicated in Table 1. Other embodiments are directed to the indicated conditions and may use other times as may be appropriate for the light source intensity and usage. The instructions may further comprise more general sterilization or sanitization process or instructions for operating the device, including deployment or movement the device members.

The light source may be UV, visible light, or a UVC light source. For instance, having an output from about 1 to about 40 Watts; artisans will immediately appreciate that all the ranges and values within the explicitly stated ranges are contemplated, e.g., 1 to about 36 Watts. In some embodiments, the UVC light source emits a peak at about 254 nm but not at about 185 nm; accordingly, some embodiments are free of light emitted at about 185 nm.

Another light source embodiment is a mixture of UVA and/or UVB and/or UVC light in the range of about 185 nm to about 365 nm. The light may come from a filtered broad spectrum light source to provide a spectrum of light within the 185-365 range, or a plurality of light sources may be used that each provide at least one peak within the 185-365 range. For instance, two or three LED light sources may be used. Moreover, the light source may exclude wavelengths outside of the 185-365 range.

Other embodiments include a timer switch in combination with deployment of the light housing, activation of the light, or user-activation of the deployment mechanism, e.g., pressing a button that lets the light housing move into the deployed position. The timer switch prevents power delivery to the light until such time as the arm travel is complete regardless of the disposition of the contacts or other circuits to activate the light. The timer switch advantageously eliminates the transmission of power while such contacts or circuits are not fully engaged.

Patents, patent applications, and publications set forth herein are hereby incorporated by reference herein to the extent they do not contradict what is explicitly disclosed herein. The embodiments describe a variety of features. In general, the features may be mixed-and-matched to make other embodiments as guided by the need to make a functional device.

TABLE 1

Time in minutes to sterilize surface according to surface type and organism*

| AREA, cm2 | DIMENSION | ITEM | Typhoid. 6000 μW/cm2 | Influenza. 6,600 μW/cm2 | Hepatitis. 8,000 μW/cm2 | Anthrax. 8,700 μW/cm2 | Mold A 10,000 μW/cm2 | Mold B. 44,000 μW/cm2 |
|---|---|---|---|---|---|---|---|---|
| 1 | (1 cm × 1 cm) | 1 Square cm | 0.02 | 0.02 | 0.02 | 0.03 | 0.03 | 0.15 |
| 72 | (18 cm × 4 cm) | Remote Control | 0.24 | 0.27 | 0.32 | 0.35 | 0.40 | 1.78 |
| 144 | (18 cm × 4c × 2) | Telephone | 0.48 | 0.53 | 0.65 | 0.70 | 0.81 | 3.56 |
| 480 | (40 cm × 32 cm) | Toilet Seat | 1.62 | 1.78 | 2.15 | 2.34 | 2.69 | 11.85 |
| 2394 | (63 cm × 38 cm) | Queen Pillow | 8.06 | 8.87 | 10.75 | 11.69 | 13.43 | 59.11 |

*Based on a UVC output of 1.5 Watts at an intensity of 4950 microwatts per square centimeter and 29700 microwatts total UV light output.

The invention claimed is:

1. A hand-held device for sanitizing a surface comprising:
a hand-held light source housing comprising an ultraviolet light source in a receptacle in the housing, with a light-emitting face of the housing having an opening for emitting light from the light source;
a covering housing rotatably mounted to the light source housing, with the covering housing having a niche for receiving the light source housing and comprising a covering face parallel to the light-emitting face of the housing;
wherein the light source in the light source housing is rotatable from a covered position inside the niche with the opening being covered by the covering housing to a deployment position outside the niche with the opening not being covered by the covering housing, with the covering face and the light-emitting face being parallel as the covering housing is rotated out of the niche to the deployment position.

2. The device of claim 1 wherein the covering housing comprises a battery and a first set of contacts and the light source housing comprises second set of contacts that contact each other upon the rotation to the deployment position to complete an electrical connection through the contacts between the battery and the light source to power the light source in the deployment position but not in the covering position.

3. The device of claim 1 further comprising an attitude sensor in a circuit for turning off the light source when the light source exceeds a predetermined angle.

4. The device of claim 3 wherein the sensor comprises a swivel ball, tilt sensor, or an accelerometer.

5. The device of claim 3 wherein the predetermined angle is 90 degrees from a horizontal position.

6. The device of claim 1 further comprising a spring that biases the light source housing to move from the covered position to the deployment position.

7. The device of claim 6 further comprising a tab that restrains the light source housing in the covered position until a user depresses a button that causes the tab to move and thereby allows the spring to move the light source housing from the covered position to the deployment position.

8. The device of claim 1 further comprising a second light source.

9. A device for sanitizing a surface comprising:
light source housing comprising a light source, with a light-emitting face of the housing having an opening for emitting light from the light source;
a covering rotatably mounted to the light source housing, with the covering having a covering face parallel to the light-emitting face of the housing;
wherein the light source housing is rotatable from a covered position with the opening being covered by the cover to a deployment position with the opening not being covered by the cover, with the covering face and the light-emitting face being parallel as the light source housing is rotated.

10. The device of claim 9 wherein the cover comprises a battery and a first set of contacts and the light source housing comprises second set of contacts that contact each other upon the rotation to the deployment position to complete an electrical connection through the contacts between the battery and the light source to power the light source in the deployment position but not in the covering position.

11. The device of claim 9 further comprising an attitude sensor in a circuit for turning off the light source when the light source exceeds a predetermined angle.

12. The device of claim 9 further comprising a spring that biases the light source housing to move from the covered position to the deployment position.

13. A method by a user of sanitizing an object comprising:
moving a light source in a light source housing from a niche inside a covering housing to a deployed position to thereby uncover the light source and to activate the light source to emit ultraviolet light from the light source housing onto the object that a user intends to sanitize, and moving the device by hand to emit the light onto the object and thereby kill organisms on the object to sanitize the object,
with the light source being recessed in a light-emitting face of the light source housing and the covering housing comprising a covering face that is parallel to and opposed to the light-emitting face in the covering position and that is parallel to the light emitting face in the deployed position.

14. The method of claim 13 wherein the light-emitting face and the covering face are parallel to each other as the light source housing is rotated from the niche to the deployment position.

15. The method of claim 13 wherein the light-emitting face and the covering face are parallel to each other as the light source housing is slid out from the niche to the deployment position.

16. The method of claim 13 wherein light source is a UVC light source that provides an output from about 1 to about 36 Watts.

* * * * *